(12) United States Patent
Salazar-Tio (10) Patent No.: US 8,861,814 B2
(45) Date of Patent: Oct. 14, 2014

(54) SYSTEM AND METHOD FOR MULTI-PHASE SEGMENTATION OF DENSITY IMAGES REPRESENTING POROUS MEDIA

(75) Inventor: Rafael Salazar-Tio, San Ramon, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 739 days.

(21) Appl. No.: 12/976,947

(22) Filed: Dec. 22, 2010

(65) Prior Publication Data

US 2012/0163688 A1 Jun. 28, 2012

(51) Int. Cl.
*G06K 9/00* (2006.01)
*G01N 23/04* (2006.01)
*G01N 15/08* (2006.01)

(52) U.S. Cl.
CPC ...... *G01N 23/046* (2013.01); *G01N 2015/0846* (2013.01); *G01N 2223/1016* (2013.01); *G01N 2223/313* (2013.01); *G01N 2223/40* (2013.01); *G01N 15/088* (2013.01)
USPC .............................. 382/128; 378/21; 600/425

(58) Field of Classification Search
CPC ................ G06T 7/0012; G06T 7/0081; G06T 2207/10072; G06T 2207/10081; G06T 2207/10076; G06T 2207/10096; G06T 2207/10101; G06T 11/003; G06T 11/008; G06T 15/08; G06T 17/00; A61B 6/032; A61B 19/50; A61B 6/649; G06K 9/432
See application file for complete search history.

(56) References Cited

U.S. PATENT DOCUMENTS

| | | | | |
|---|---|---|---|---|
| 5,187,658 A | * | 2/1993 | Cline et al. | 382/128 |
| 5,452,367 A | * | 9/1995 | Bick et al. | 382/128 |
| 5,699,799 A | * | 12/1997 | Xu et al. | 600/407 |
| 5,832,134 A | * | 11/1998 | Avinash et al. | 382/257 |
| 5,891,030 A | * | 4/1999 | Johnson et al. | 600/407 |
| 5,923,775 A | * | 7/1999 | Snyder et al. | 382/172 |
| 5,987,094 A | * | 11/1999 | Clarke et al. | 378/62 |
| 6,044,125 A | * | 3/2000 | Flohr et al. | 378/4 |
| 6,047,039 A | * | 4/2000 | Flohr | 378/4 |
| 6,047,090 A | * | 4/2000 | Makram-Ebeid | 382/257 |
| 6,385,479 B1 | * | 5/2002 | Sibbitt et al. | 600/410 |
| 6,731,782 B2 | * | 5/2004 | Ashton | 382/131 |

(Continued)

OTHER PUBLICATIONS

M.A. Knackstedt, Properties of reservoir core derived from 3D images, 2004, Society of Petroleum Engineers, Inc.*

(Continued)

*Primary Examiner* — Manav Seth
(74) *Attorney, Agent, or Firm* — Albert K. Shung (57) ABSTRACT

A system and method for multi-phase segmentation of noisy 3D x-ray tomography images representative of porous material minimizing data smoothing which processes 3D x-ray tomography images to obtain a standardized intensity image, segments the standardized intensity image into at least 3 phases, calculates volumetric fractions and spatial distributions of the segmented phases and compares them with target values, and if the calculated fractions are not close enough to the target values, repeats the necessary segmentation steps until the calculated volumetric fractions are within a given tolerance to the target values. The segmentation steps include computing a median/mean-filtered-gradient image of the standardized intensity image, creating an intensity vs. gradient graph from the median/mean-filtered-gradient image and the standardized intensity image, partitioning the intensity vs. gradient graph into at least 3 regions, using thresholds defining the regions to segment the standardized grey scale image to create a segmented image, and applying a despeckler filter to remove noise in the segmented image.

24 Claims, 4 Drawing Sheets

(56) References Cited

U.S. PATENT DOCUMENTS

| | | |
|---|---|---|
| 6,747,697 B1 * | 6/2004 | Lin et al. .................... 348/246 |
| 7,689,021 B2 * | 3/2010 | Shekhar et al. ............. 382/131 |
| 7,869,565 B2 * | 1/2011 | Wood et al. ................... 378/53 |
| 8,155,377 B2 * | 4/2012 | Dvorkin et al. ............. 382/100 |
| 8,750,615 B2 * | 6/2014 | Rollins et al. ............... 382/173 |
| 2005/0201618 A1 | 9/2005 | Tek |
| 2006/0018526 A1 | 1/2006 | Avinash |
| 2008/0255049 A1 * | 10/2008 | Sumner et al. ................. 514/12 |
| 2008/0292171 A1 | 11/2008 | Bruder et al. |
| 2009/0082660 A1 | 3/2009 | Rahn et al. |
| 2009/0103677 A1 | 4/2009 | Wood et al. |
| 2009/0154787 A1 | 6/2009 | Bertram et al. |
| 2009/0274354 A1 | 11/2009 | Ng et al. |

OTHER PUBLICATIONS

S. Youssef, et al., "High Resolution μ-CT Combined to Numerical Models to Assess Electrical Properties of Bimodal Carbonates," paper prepared for presentation at the International Symposium of the Society of Core Analysts held in Abu Dhabi, UAE Oct. 29-Nov. 2, 2008.

E. Throng et al., "A Methodology to Segment X-Ray Tomographic Images of Multiphase Porous Media: Application to Building Stones," hal-00260435, version 1, Mar. 4, 2008.

PCT/US2011/052366, International Search Report and Written Opinion, filing date Sep. 20, 2011, 8 pages.

\* cited by examiner

SYSTEM AND METHOD FOR MULTI-PHASE SEGMENTATION OF DENSITY IMAGES REPRESENTING POROUS MEDIA

FIELD OF THE INVENTION

The present invention relates generally to methods and systems for multi-phase segmentation of density images representing porous media and, in particular, methods and systems for multi-phase segmentation of noisy 3D x-ray tomography images representing rock samples.

BACKGROUND OF THE INVENTION

Proper development of hydrocarbon reservoirs requires accurate reservoir simulation. Accurate reservoir simulation may be achieved with proper modeling of the porosity and the connectivity of the pore structure of the rocks that form the reservoir at different scales, including grain-pore levels. The porosity distribution and its connectivity will affect not only the amount of hydrocarbons in the reservoir, but also how readily the hydrocarbons may flow through the reservoir.

In rocks that make up a hydrocarbon reservoir, grain minerals are surrounded by open space in the form of interconnected pores or a pore network. The texture of the pore network, which includes connectivity, range of pore sizes and average pore size, is a function of the type of rock. Pore sizes can range in size from a few millimeters to a few nanometers. Some rocks have a narrow range of pore sizes, such as clastic rocks with well sorted grains, while others have a wide range, such as some carbonate rocks which may have both millimeter size vugs and micro-porosity too (pores with diameters between 10-100 nanometers). High resolution 2D imaging techniques, such as Back Scattering Electron Microscopy (BSEM), can image down to 10 nanometer resolution, but the connectivity of the pore network needs to be characterized in 3D.

One tool that can be used to generate data that can be used to characterize the pore connectivity of a rock sample is 3D x-ray micro-tomography. X-ray tomography images are monochromatic and the local intensity in the images is proportional to the local density of the material. In x-ray tomography, an x-ray source, a rotation stage and a detector are used to create 2D projections at several orientations of the rock sample respect to the source-detector line, and then a reconstruction algorithm is used to produce a 3D density volume. This is a non-invasive technique, and the data generated is typically noisy depending on the flux of detected photons, particularly if the scanning is done too quickly, if the rock is particularly dense, or if the quality of the x-ray source is not adequate. The resolution of the images or pixel size depends on the spot-size of the x-ray source and on the geometrical or optical magnification system used on the micro-tomography scanner. Typically, the spatial resolution on micro-tomography using geometrical magnification is 2-3 µm/pixel, while systems using optical magnification can go down to about 0.5 µm/pixel.

At any of these resolutions, there may be still some un-resolvable features, such as micro-porosity in carbonates or in clay. In order to model pore connectivity, it is required to segment or identify the pore pixels. However, pixels containing sub-resolution pores cannot be labeled pore, but can be label "sub-resolution porosity" and a micro-porosity value can be associated with the intermediate grey in the intensity images. Other phases of interest can also be segmented based on the grey intensity of the images, such as fluids (brine, oil), bitumen, and relevant minerals (clays, feldspars, etc). Current segmentation methods of the 3D x-ray micro-tomography images into phases are limited mainly by the interplay between intensity contrast for phases to be segmented and the signal-to-noise level of the data.

Current segmentation methods that focus on porosity characterization include 2-phase segmentations (pore/solid), and 3-phase segmentations (pore/sub-resolution-porosity/solid) using thresholds, smoothing filters, and morphological transformations (watershed, active contour, dilation/erosion methods). The 2-phase segmentation method divides the images into solid or pore pixels, erroneously labeling the sub-resolution porosity pixels as pore or solid, therefore, accounting only for pores of resolvable size. Current 2-phase and 3-phase segmentation using thresholds determined from the x-ray tomography images result in segmented images that have a characteristic "salt-and-pepper" noise that can be minimized by applying smoothing algorithms prior to segmentation, such as mean/median filters and anisotropy diffusion filters. The smoothing filters effectively reduce the spatial resolution of the image because they mix information of nearby pixels, which results in increasing the total sub-resolution porosity fraction. Additional lost of resolution and smoothing results from the application of subsequent morphological transformations in the current methods. Sometimes a distinguishable artificial length scale can be introduced when using smoothing filters. Smoothing can also underestimate inter-phase surface roughness and affect final simulation results, such as increasing fluid flow permeability.

For these reasons, current segmentation methods cannot be relied on to properly segment the x-ray tomography images into a representation that accurately depicts the resolvable porosity, the un-resolvable porosity, and the solid phases at the original pixel resolution of the tomogram; current methods have a larger, poorer resolution. With these inaccurate segmentation methods, the resulting models for connectivity of the pore networks may not be precise enough, and scaled properties used in reservoir simulation will not be correct.

SUMMARY OF THE INVENTION

Described herein are implementations of various approaches for multi-phase segmentation of noisy density images representing porous media while minimizing data smoothing. According to one aspect of the present invention, the method may include processing 3D x-ray tomography images to obtain a standardized intensity image, segmenting the standardized intensity image into at least 3 phases, determining volumetric fractions and spatial distributions of the segmented phases, and comparing them with target values. If the determined volumetric fractions are within a predetermined tolerance to the target values, the segmented image is considered correct and may be used as a pore network for reservoir simulation. If the determined fractions are not close enough to the target values, the method may include repeating the segmentation, determination, and comparison steps until the determined volumetric fractions are within a given tolerance to the target values.

The processing step may include the steps of stitching, rotating and cropping the 3D x-ray tomography images, spatially equalizing the 3D x-ray tomography images, and/or selecting a sufficient grey scale dynamic range and resampling the 3D x-ray tomography images to a lower bit-rate. In the case of exceptionally noisy 3D x-ray tomography images, a median/mean filter with a selectable radius no greater than 2 pixels may be applied prior to segmentation. A small median/mean filter will help to reduce the noise level without introducing smoothing artifacts.

The segmentation step may include the steps of computing a median/mean-filtered-gradient image of the standardized intensity image, creating an intensity vs. gradient graph from the median/mean-filtered-gradient image and the standardized intensity image, partitioning the intensity vs. gradient graph into at least 3 regions, using thresholds defining the regions to segment the standardized grey scale image to create a segmented image, and applying a despeckler filter to remove noise in the segmented image. In one embodiment, the phases may include a pore phase, a sub-resolution-porosity, and a solid phase. In another embodiment, the phases may also include fluids such as brine or oil, bitumen, and/or relevant minerals such as clays or feldspars.

Once the segmentation of the image is complete, volumetric fractions of the phases, for example the porosity and sub-resolution-porosity fractions, and the spatial distribution/spatial correlation of the phases is calculated. These calculations are compared to target values and if they within a predetermined tolerance (or range), the segmentation is repeated from the partitioning step onward. The target values may be determined from Quantitative X-Ray Diffraction (XRD), Mercury Injection Capillary Pressure (MICP), Back Scattering Electron Microscopy (BSEM), and/or Quantitative Mineralogy Surface Electron Microscopy (QEMSCAN).

The present invention may also be practiced as a system, the system including a data source having data representative of 3D x-ray tomography images, at least one computer processor being configured to communicate with the data source and to execute computer program modules including a processing module, a segmentation module, a phase fraction determination module, and a comparison module. The system may also include a user interface.

The processing module of the system may execute the steps of stitching, rotating and cropping the 3D x-ray tomography images, spatially equalizing the 3D x-ray tomography images, and/or selecting a sufficient grey scale dynamic range and resampling the 3D x-ray tomography images to a lower bit-rate. In the case of exceptionally noisy 3D x-ray tomography images, the processing module may apply a median/mean filter with a selectable radius no greater than 2 pixels.

The segmentation module of the system may execute computing the steps of a median/mean-filtered-gradient image of a standardized intensity image, creating an intensity vs. gradient graph from the median/mean-filtered-gradient image and the standardized intensity image, partitioning the intensity vs. gradient graph into at least 3 regions, using thresholds defining the regions to segment the standardized intensity image to create a segmented image, and applying a despeckler filter to remove noise in the segmented image. The segmentation module may output at least 3 phases that include a pore phase, a sub-resolution-porosity, and a solid phase. The phases may also include fluids such as brine or oil, bitumen, and/or relevant minerals such as clays or feldspars.

The phase fraction determination module may calculate, for example, porosity and sub-resolution-porosity fractions and spatial correlations of the phases. In one embodiment, the determined phase fractions would be input to the comparison module, which would compare the determined properties from the property calculation module against target values determined from, for example, Quantitative X-Ray Diffraction (XRD), Mercury Injection Capillary Pressure (MICP), Back Scattering Electron Microscopy (BSEM), and/or Quantitative Mineralogy Surface Electron Microscopy (QEMSCAN). If the calculated values are not within a predetermined tolerance of the target values, the segmentation module begins the partitioning step and the segmentation step repeats until the determined values are within the predetermined tolerance.

In addition, the present invention encompasses an article of manufacture including a computer readable medium having computer readable code, which will allow a computer to implement a method for segmentation of noisy 3D x-ray tomography images representative of porous material minimizing data smoothing including processing 3D x-ray tomography images to obtain a standardized intensity image, segmenting the standardized intensity image into at least 3 phases, calculating volumetric fractions and spatial distribution of the segmented phases and comparing them with target values, and repeating the segmentation until the calculated volumetric fractions are within a given tolerance to the target values.

The above summary section is provided to introduce a selection of concepts in a simplified form that are further described below in the detailed description section. The summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

These and other features of the present invention will become better understood with regard to the following description, claims and accompanying drawings where:

DETAILED DESCRIPTION OF THE INVENTION

The present invention may be described and implemented in the general context of a system and computer methods to be executed by a computer. Such computer-executable instructions may include programs, routines, objects, components, data structures, and computer software technologies that can be used to perform particular tasks and process abstract data types. Software implementations of the present invention may be coded in different languages for application in a variety of computing platforms and environments. It will be appreciated that the scope and underlying principles of the present invention are not limited to any particular computer software technology.

Moreover, those skilled in the art will appreciate that the present invention may be practiced using any one or combination of hardware and software configurations, including but not limited to a system having single and/or multiple processor computers, hand-held devices, programmable consumer electronics, mini-computers, mainframe computers, and the like. The invention may also be practiced in distributed computing environments where tasks are performed by servers or other processing devices that are linked through a one or more data communications network. In a distributed computing environment, program modules may be located in both local and remote computer storage media including memory storage devices. The present invention may also be practiced as part of a down-hole sensor or measuring device or as part of a laboratory measuring device.

Also, an article of manufacture for use with a computer processor, such as a CD, pre-recorded disk or other equivalent devices, may include a computer program storage medium and program means recorded thereon for directing the computer processor to facilitate the implementation and practice of the present invention. Such devices and articles of manufacture also fall within the spirit and scope of the present invention.

Referring now to the drawings, embodiments of the present invention will be described. The invention can be implemented in numerous ways, including, for example, as a system (including a computer processing system), a method (including a computer implemented method), an apparatus, a computer readable medium, a computer program product, a graphical user interface, a web portal, or a data structure tangibly fixed in a computer readable memory. Several embodiments of the present invention are discussed below. The appended drawings illustrate only typical embodiments of the present invention and therefore are not to be considered limiting of its scope and breadth.

The present invention relates to segmenting noisy density images representative of porous media into images with multiple phases while minimizing data smoothing. In the case of noisy 3D x-ray tomography images representative of rock samples while minimizing data smoothing, the inventor has determined that an iterative method using the intensity and the gradient of the 3D data to determine thresholds for segmentation followed by a despeckler filter may allow accurate modeling of several phases at the original resolution of the tomogram, including, by way of example and not limitation, a solid phase, a pore phase, and a sub-resolution-porosity phase.

Figure 1:
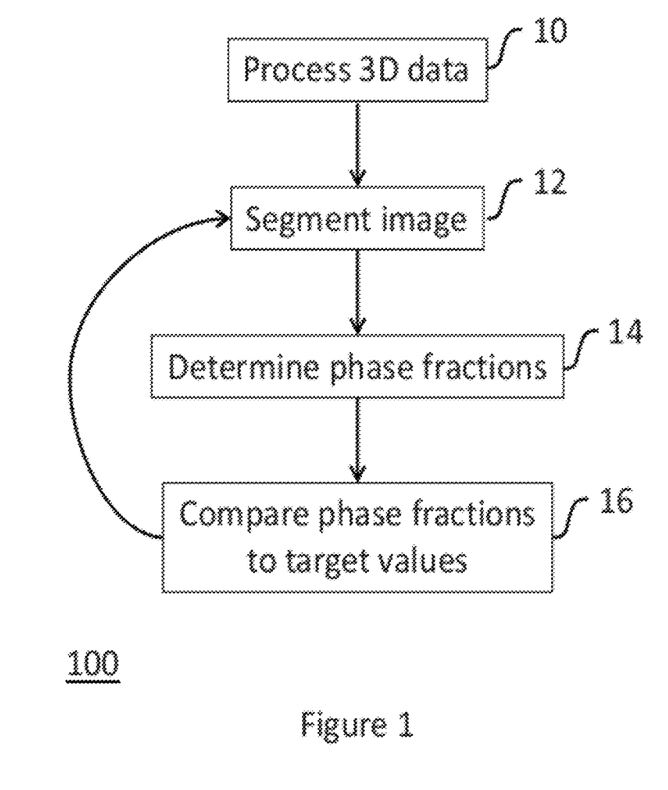
FIG. 1 is a flowchart illustrating a method in accordance with an embodiment of the invention.

In this regard, an example of a method 100 in accordance with the present invention is illustrated in the flowchart of FIG. 1. The method may use noisy 3D density images, typically from x-ray tomography. Although there is calibration for the intensity values (CT number) to some standards, different tomography systems produce different images. 3D x-ray tomography images are generated by reconstruction of a set of 2D projections using the appropriated algorithm for the different tomography system (cone, fan, helical, or parallel beam). Detectors can differ from flat panels to charge-coupled device (CCD) cameras with different specifications, like grey scale depth and grid size. Sources can be also different, from laboratory x-ray tubes at different power, spot size, hardware filters for beam hardening (uneven intensity) to parallel beam synchrotron sources at different energies. Simple systems use only geometric magnification in comparison with optical magnification after scintillators converts x-ray to optical range. Different parameters can be set, like exposure time and image averaging, software filters for rings removal or noise reduction. Also, different tomography modes are possible: absorption mode or phase contrast related with parallel beam or high resolution imaging. All of these differences may have an effect on the x-ray tomography images and may be handled via the processing in step 10 prior to segmentation.

3D x-ray tomography devices also have different resolution depending on the magnification system used. Typically the spatial resolution on x-ray micro-tomography using geometrical magnification is 2-3 µm/pixel, while systems using optical magnification can go down to about 0.5 µm/pixel. At any of these resolutions, there may be still some un-resolvable features, such as micro-porosity in carbonates or in clay. In order to characterize the mechanisms for fluid distribution and fluid flow for a particular rock type, the tomogram resolution should be selected such that the primary interconnected porosity or pore network is properly imaged. Depending on the rock type, the selected resolution may vary significantly, from 0.1 µm/pixel to 10 µm/pixel. The secondary porosity below the selected resolution should not be needed to characterize pore connectivity and fluid flow. For some rock types and/or tomography systems, it may not possible to achieve the required resolution, in which case the value of x-ray micro-tomography imaging for pore scale characterization would be low.

The processing in step 10 of the noisy density images may be used to standardize the data to create a grey scale image suitable for segmentation. In the case of noisy 3D x-ray tomography images, the processing may handle the issues caused by different settings of the different x-ray tomography devices to create a standardized intensity image.

One processing technique that may be done is stitching tomograms, rotating, and cropping the data to create a volume of an orientation and size that is well-suited to further processing and segmentation. In one embodiment, this volume would be a rectangular prism containing the region of interest (ROI) representative of the rock texture to be characterized.

Another processing technique might be spatial equalization of the 3D density images. In the case of x-ray tomography images, some non-monochromatic sources can produce a beam hardening effect which shows as an uneven intensity in different image regions. In one embodiment, the spatial equalization may be done by focusing on one mineral phase that should be homogeneous along the image, computing the correction factors necessary to achieve homogeneity, and applying the correction factors to the whole image.

X-ray tomography images may be acquired in either phase contrast mode or absorption mode. If the images were acquired in phase contrast mode, they may be converted to absorption mode. The absorption mode images are preferred for the present invention.

In one embodiment, further processing may be done to select a sufficient dynamic range in the grey scale domain for the intensity, where there is enough contrast between the lowest and highest relevant features in the ROI. For example, if the 3D density images have been recorded at 16-bit, it may be desirable to select a sufficient grey scale range and resample it at 8-bit.

In some cases, the x-ray tomography images may be extremely noisy. This may occur if the settings for exposure time are unreasonable low for the density of the rock sample. In the case of extremely noisy data, another processing technique may be applying a small radius median/mean filter to the noisy data. In one embodiment, the filter would have a radius no larger than 2 pixels.

Each of the processing techniques described as possible options for step 10 are optional and should be selected based on the available data. The techniques can be applied in any order. The techniques described above are examples and are not meant to be limiting; it will be appreciated that there are other processing steps that may also be applied that fall within the scope of the present invention. An example of a standardized intensity image may be seen as part of the series of examples 300 in FIG. 3, where a 2D slice from a 3D x-ray micro-tomography standardized intensity image is seen in panel 30.

Figure 2:
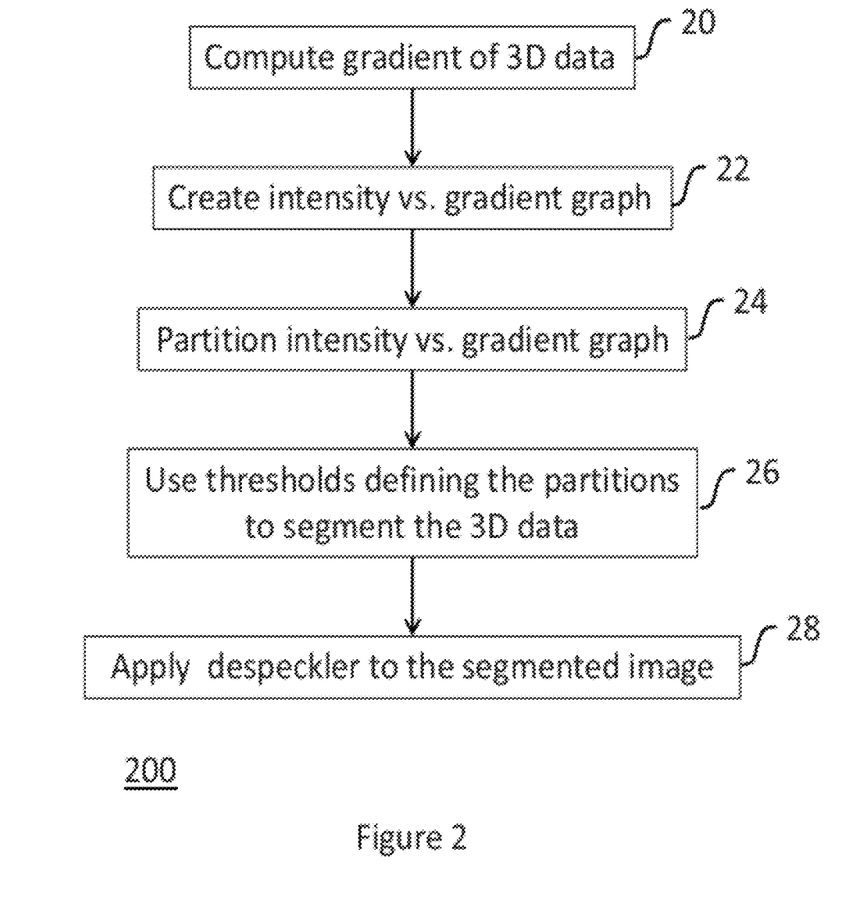
FIG. 2 is a flowchart illustrating the details of step 12 in FIG. 1.

From the standardized intensity image, a segmented image is created in step 12 of FIG. 1. Multiple phases may be segmented, including a solid phase, a pore phase, and a sub-resolution-porosity phase. Other possible phases include but are not limited to fluids (brine, oil), bitumen, and relevant minerals (clays, feldspars, etc). The method of segmentation in the present invention does not require smoothing filters as do current methods, and is thus more accurate, within the original pixel resolution of the tomogram, in the phases and the spatial correlations of the phases. The present invention minimizes smoothing effects so that the resolution of the segmented image is as high as possible, unlike current methods. FIG. 2 shows the details of the segmentation.

In FIG. 2, the segmentation method 200 is described. At step 20, the present invention computes a median/mean-filtered-gradient of the standardized intensity image resulting from step 10 in FIG. 1. The gradient of a noisy image is generally noisier, so we calculate instead the gradient of a smoothed out version of the intensity image. We still use the original non-smoothed intensity image for the main segmentation step. An example of the gradient can be seen in FIG. 3, panel 31, which is a 2D slice of the 3D volume gradient. The gradient and the standardized intensity image are then used to create an intensity versus gradient graph at step 22. Each image pixel has associated two values, the intensity and the gradient, which are used to locate the pixel in this graph. This graph may then be partitioned into regions that correspond to multiple phases at step 24. An example of a partitioned intensity versus gradient graph can be seen in FIG. 3, panel 32.

The partitioning of the intensity versus gradient graph may include a partition for the pore phase, which will include any pixel with intensity below a threshold value, such as line 33 in FIG. 3, regardless of its gradient value. It also may include a partition for sub-resolution-porosity phase, typically located in the intermediate grey intensity region, and low gradient region, which will include pixels with intensities between threshold values such as line 33 and line 35 in FIG. 3, and gradient values below a threshold value such as line 34 in FIG. 3, trying to rule out the pixels at the pore/solid sharp transition interfaces. Other phases, such as fluids, clay, bitumen, or other minerals may also be partitioned with threshold values for intensity and gradient. In the case of the 3-phase segmentation focused on porosity characterization (pore/sub-resolution-porosity/solid) shown in panel 32, the remaining pixels are marked as solid. The determination of the proper locations for the partitions can be aided with an overlapping 1D-histogram of the intensity, as shown in FIG. 3 as curve 36.

In step 26 of FIG. 2, the thresholds defining each of the partitions set in step 24 are used to segment the standardized intensity image. A new image is created by segmentation where each new pixel has a phase-label value, for example, pore (0), sub-resolution-porosity (1), and solid (2). The phase-label for each pixel is determined by the location of that pixel in the intensity versus gradient graph, and in which partition region the pixel falls. An example of a segmented image can be seen in FIG. 3, panel 37, which is a 2D slice of the segmented volume.

Figure 3:
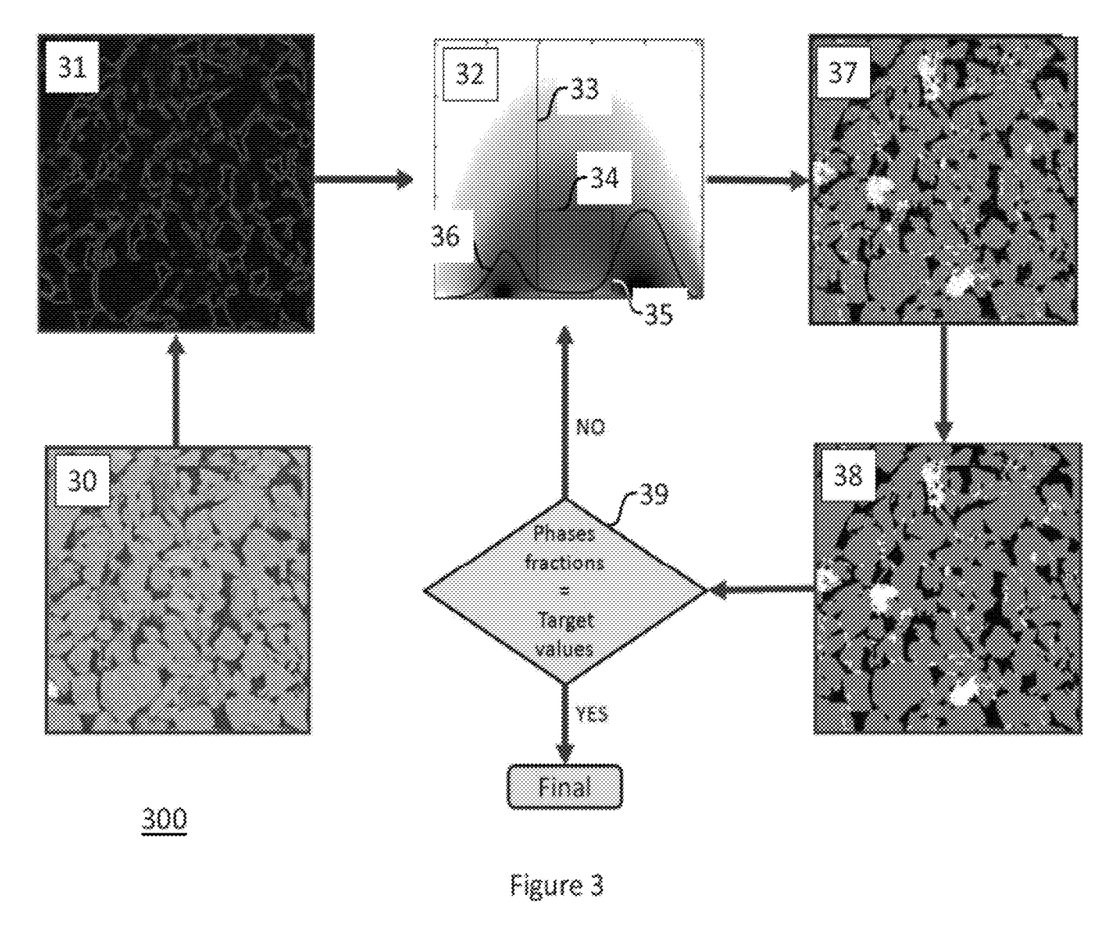
FIG. 3 shows a 2D slice of x-ray tomography images and its changes as it goes through the segmentation method.

Since no smoothing filter is used in the method of the present invention, the segmented image from step 26 may contain small, scattered, unconnected volumes of a phase different than the surrounding background phase, which are commonly referred to as "salt-and-pepper" noise, as can be seen in FIG. 3, panel 37. In the present invention, this kind of noise is removed after the segmentation step by applying a despeckler filter individually to each phase in step 28. The despeckler filter looks for unconnected volumes of other phases inside a main phase. If these volumes are below a user-defined size, typically between 10 and 100 pixels, the unconnected volume is redefined as part of the larger phase surrounding it. This limit-size condition is used to define what is considered noise and what real features are. An example of a despeckled segmented image can be seen in FIG. 3, panel 38.

Referring again to FIG. 1, in step 14 the segmented image may be used to determine volumetric phase fractions for phases such as pore and sub-resolution-porosity or for other segmented phases, such as fluids, clay, bitumen, or other minerals. In step 16, these determined volumetric phase fractions are compared to target values. This step is also represented in FIG. 3 as step 39. The target values may be obtained from laboratory measurements on sister rock samples, for example Quantitative X-Ray Diffraction (XRD), Mercury Injection Capillary Pressure (MICP), Back Scattering Electron Microscopy (BSEM), and/or Quantitative Mineralogy Surface Electron Microscopy (QEMSCAN). If the phase fractions determined from the segmented image are within a predetermined tolerance to the target values, for example in one embodiment within 5% of the target, the segmented image is accepted as correct and the pore network it represents may be used for reservoir simulation. If the determined phase fractions are not close enough to the target fractions, the method returns to step 12 in FIG. 1 where the segmentation is now done as steps 24-28 in FIG. 2 (also shown as returning to panel 32 in FIG. 3), and repeats steps 14 and 16 from FIG. 1 until the determined phase fractions are within the tolerance.

Figure 4:
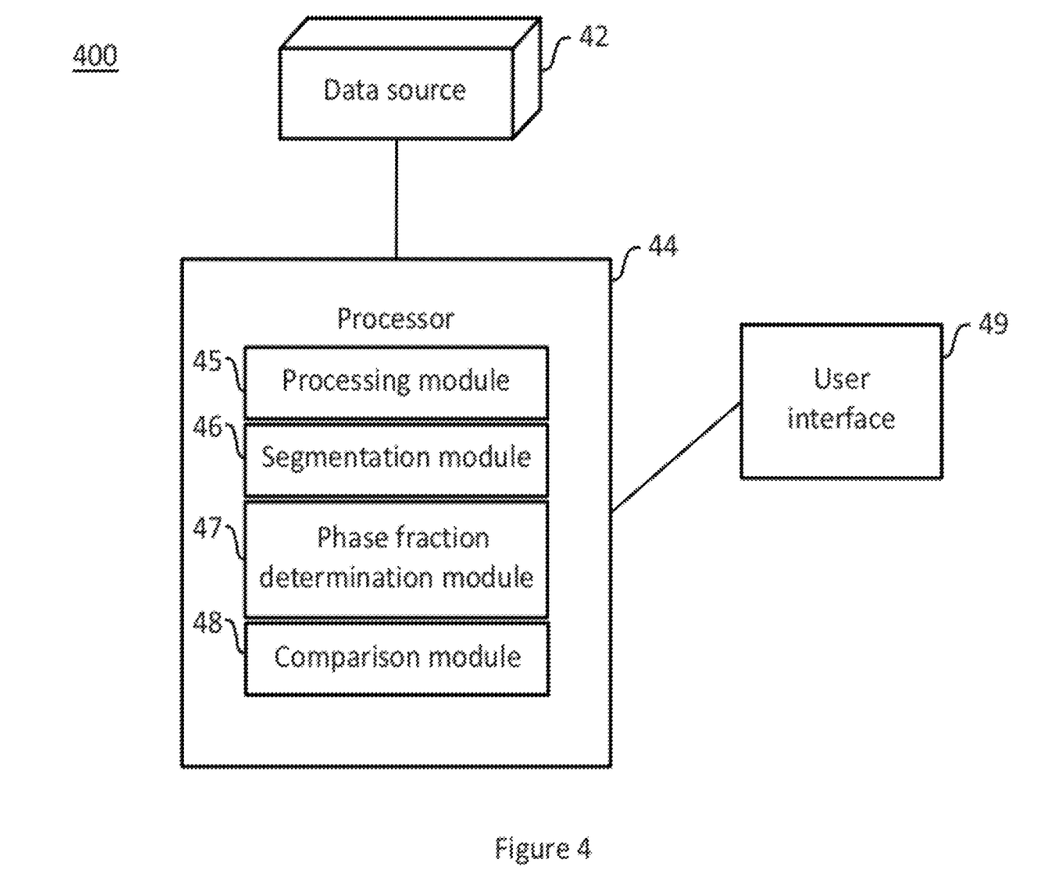
FIG. 4 schematically illustrates a system for performing a method in accordance with an embodiment of the invention.

A system 400 for performing the method is schematically illustrated in FIG. 4. The system includes a data source 42 which may include, among others, a data storage device or computer memory. The stored noisy density data, which may be 3D x-ray tomography data, may be made available to a processor 44, such as a programmable general purpose computer. The processor 44 is configured to execute a processing module 45 to prepare a standardized intensity image, a segmentation module 46 to segment the intensity image into multiple phases, a phase fraction determination module 47 to determine phase fractions including, for example, the porosity fraction and the sub-resolution-porosity fraction, and a comparison module 48 to compare the phase fractions from the phase fraction determination module to target values. If the comparison module finds that the comparison fails, it can restart the segmentation module. The system may include interface components such as user interface 49, and is used to implement the above-described transforms in accordance with embodiments of the invention. The user interface 49 may be used both to display data and processed data products and to allow the user to select among options for implementing aspects of the method. By way of example and not limitation, the segmented image and determined phase fractions computed on the processor 44 may be displayed on the user interface 49, stored on the data storage device or memory 42, or both displayed and stored. The multi-phase image and determined phase fractions may be used as input to reservoir simulation.

While in the foregoing specification this invention has been described in relation to certain preferred embodiments thereof, and many details have been set forth for purpose of illustration, it will be apparent to those skilled in the art that the invention is susceptible to alteration and that certain other details described herein can vary considerably without departing from the basic principles of the invention. In addition, it should be appreciated that structural features or method steps shown or described in any one embodiment herein can be used in other embodiments as well.

What is claimed is:

1. A computer-implemented method for multi-phase segmentation of noisy 3D x-ray tomography images representative of porous material, the method comprising:

a. processing 3D x-ray tomography images to obtain a standardized intensity image, wherein the processing comprises:
   i. stitching, rotating and cropping the 3D x-ray tomography images;
   ii. spatial equalization of the 3D x-ray tomography images; and
   iii. selecting a sufficient grey scale dynamic range and optionally resampling the 3D x-ray tomography images to a lower bit-rate.;
b. segmenting the standardized intensity image into at least 3 phases;
c. determining volumetric fractions and spatial distributions of the at least 3 segmented phases; and
d. comparing the determined volumetric fractions with target values.

2. A system for multi-phase segmentation of noisy 3D x-ray tomography images representative of porous material, the system comprising:
a. a data source containing 3D x-ray tomography images;
b. at least one computer processor being configured to communicate with the data source and to execute computer program modules, the computer modules comprising:
   i. a processing module, wherein the processing module executes:
      stitching, rotating and cropping the 3D x-ray tomography images;
      spatial equalization of the 3D x-ray tomography images; and
      selecting a sufficient dynamic range and optionally resampling the 3D x-ray tomography images to a lower bit-rate.;
   ii. a segmentation module;
   iii. a phase fraction determination module; and
   iv. a comparison module.

3. A computer-implemented method for multi-phase segmentation of noisy 3D x-ray tomography images representative of porous material, the method comprising:
a. processing 3D x-ray tomography images to obtain a standardized intensity image;
b. segmenting the standardized intensity image into at least 3 phases to create a segmented image, wherein segmenting the standardized intensity image comprises applying a despeckler filter to remove noise in the segmented image;
c. determining volumetric fractions and spatial distributions of the at least 3 segmented phases; and
d. comparing the determined volumetric fractions with target values, wherein if the determined volumetric fractions are not within a predetermined tolerance to the target values, the method further comprises repeating the segmenting step, the determining step and the comparing step until the determined volumetric fractions are within a predetermined tolerance to the target values.

4. The method of claim 3, wherein the processing comprises:
a. stitching, rotating and cropping the 3D x-ray tomography images;
b. spatial equalization of the 3D x-ray tomography images; and
c. selecting a sufficient grey scale dynamic range and optionally resampling the 3D x-ray tomography images to a lower bit-rate.

5. The method of claim 4, further comprising applying a median/mean filter with a selectable radius.

6. The method of claim 5, wherein the selectable radius is no greater than 2 pixels.

7. The method of claim 4, further comprising converting a phase contrast mode to an absorption mode.

8. The method of claim 3, the segmenting the standardized intensity image comprising:
a. computing a median/mean-filtered-gradient image of the standardized intensity image;
b. creating an intensity vs. gradient graph from the median/mean-filtered-gradient image and the standardized intensity image;
c. partitioning the intensity vs. gradient graph into at least 3 regions; and
d. using thresholds defining the at least 3 regions to segment the standardized grey scale image to create the segmented image.

9. The method of claim 3, the at least 3 phases representing a pore phase, a sub-resolution-porosity phase, and a solid phase.

10. The method of claim 3, the at least 3 phases representing a pore phase, a sub-resolution-porosity phase, a solid phase, fluid phase, a bitumen phase, and/or phases of relevant minerals.

11. The method of claim 3, wherein the determined volumetric fractions include porosity and sub-resolution-porosity fractions and the spatial distribution includes spatial correlation of the at least 3 phases.

12. The method of claim 3, wherein the target values may be from Quantitative X-Ray Diffraction (XRD), Mercury Injection Capillary Pressure (MICP), Back Scattering Electron Microscopy (BSEM), and/or Quantitative Mineralogy Surface Electron Microscopy (QEMSCAN).

13. A system for multi-phase segmentation of noisy 3D x-ray tomography images representative of porous material, the system comprising:
a. a data source containing 3D x-ray tomography images;
b. at least one computer processor being configured to communicate with the data source and to execute computer program modules, the computer modules comprising:
   i. a processing module;
   ii. a segmentation module to create a segmented image, wherein the segmentation module executes segmenting the standardized intensity image into at least 3 phases to create a segmented image
   iii. a phase fraction determination module, wherein the phase fraction module executes determining volumetric fractions and spatial distributions of the at least 3 segmented phases; and
   iv. a comparison module, wherein the comparison module executes comparing the determined volumetric fractions with target values, wherein if the determined volumetric fractions are not within a predetermined tolerance to the target values, the method further comprises repeating the segmenting step, the determining step and the comparing step until the determined volumetric fractions are within a predetermined tolerance to the target values.

14. The system of claim 13, further comprising a user interface.

15. The system of claim 13, wherein the processing module executes:
a. stitching, rotating and cropping the 3D x-ray tomography images;
b. spatial equalization of the 3D x-ray tomography images; and c. selecting a sufficient dynamic range and optionally resampling the 3D x-ray tomography images to a lower bit-rate.

16. The system of claim 15, wherein the processing module further executes applying a small median/mean filter with a selectable radius.

17. The system of claim 16, wherein the radius is no greater than 2 pixels.

18. The system of claim 17, wherein the processing module further executes converting a phase contrast mode to an absorption mode.

19. The system of claim 17, wherein the segmentation module executes:
   a. computing a median/mean-filtered-gradient image of a standardized intensity image;
   b. creating an intensity vs. gradient graph from the median/mean-filtered-gradient image and the standardized intensity image;
   c. partitioning the intensity vs. gradient graph into the at least 3 regions;
   d. using thresholds defining the at least 3 regions to segment the standardized intensity image to create a segmented image; and
   e. applying a despeckler filter to remove noise in the segmented image.

20. The system of claim 13, wherein the segmentation module outputs at least 3 phases that represent a pore phase, a sub-resolution-porosity, and a solid phase.

21. The system of claim 13, wherein the segmentation module outputs at least 3 phases that represent a pore phase, a sub-resolution-porosity, a solid phase, a fluid phase, a bitumen phase, and/or phases of relevant minerals.

22. The system of claim 13, wherein the phase fraction determination module calculates porosity and sub-resolution-porosity fractions and spatial correlations of the phases.

23. The system of claim 13, wherein the comparison module compares calculated properties from the property calculation module against target values from Quantitative X-Ray Diffraction (XRD), Mercury Injection Capillary Pressure (MICA), Back Scattering Electron Microscopy (BSEM), and/or Quantitative Mineralogy Surface Electron Microscopy (QEMSCAN).

24. An article of manufacture including a non-transitory computer readable medium having computer readable code on it, the computer readable code being configured to implement a method for segmentation of noisy 3D x-ray tomography images representative of porous material, the method comprising:
   a. processing 3D x-ray tomography images to obtain a standardized intensity image;
   b. segmenting the standardized intensity image into at least 3 phases to create a segmented image, wherein segmenting the standardized intensity image comprises applying a despeckler filter to remove noise in the segmented image;
   c. determining volumetric fractions and spatial distribution of the at least 3 segmented phases; and
   d. comparing the determined volumetric fractions with target value, wherein if the determined volumetric fractions are not within a predetermined tolerance to the target values, the method further comprises repeating the segmenting step, the determining step and the comparing step until the determined volumetric fractions are within a predetermined tolerance to the target values.

* * * * *